(12) United States Patent
Abo

(10) Patent No.: US 6,716,633 B2
(45) Date of Patent: Apr. 6, 2004

(54) BLOOD CELL DETECTOR, BLOOD ANALYZER AND BLOOD ANALYZING METHOD USING THE DETECTOR

(75) Inventor: Mitsuru Abo, Miki (JP)

(73) Assignee: Sysmex Corporation, Hyogo (JP)

(*) Notice: Subject to any disclaimer, the term of this patent is extended or adjusted under 35 U.S.C. 154(b) by 226 days.

(21) Appl. No.: 09/954,057

(22) Filed: Sep. 18, 2001

(65) Prior Publication Data

US 2002/0034824 A1 Mar. 21, 2002

(30) Foreign Application Priority Data

Sep. 18, 2000 (JP) .................................. 2000-282458

(51) Int. Cl.[7] ......................... G01N 33/48; G01N 31/00
(52) U.S. Cl. ........................ 436/63; 436/10; 436/66; 436/52; 436/54; 436/149; 436/150; 436/164; 436/165; 422/73; 422/82.01; 422/82.02; 422/82.05; 422/68.1; 435/2; 435/29; 435/39
(58) Field of Search ..................... 436/10, 63, 66, 436/52, 54, 149, 150, 164, 165, 180; 422/73, 81, 82.01, 82.02, 82.05, 82.09, 100, 68.1; 435/2, 29, 39, 283.1, 287.1, 287.3, 288.7

(56) References Cited

U.S. PATENT DOCUMENTS

| | | | |
|---|---|---|---|
| 3,921,066 A | * 11/1975 | Angel et al. | 377/12 |
| 4,078,211 A | 3/1978 | Longman, Jr. | |
| 4,729,876 A | * 3/1988 | Hennessy et al. | 422/103 |
| 5,150,037 A | * 9/1992 | Kouzuki | 324/71.4 |
| 5,166,537 A | * 11/1992 | Horiuchi et al. | 250/573 |
| 5,266,269 A | * 11/1993 | Niiyama et al. | 422/73 |
| 5,380,491 A | * 1/1995 | Carver et al. | 422/73 |
| 5,731,211 A | * 3/1998 | Ohlin | 436/179 |
| 6,555,065 B1 | * 4/2003 | Melet | 422/73 |

FOREIGN PATENT DOCUMENTS

| | | | |
|---|---|---|---|
| EP | 335789 | * | 10/1989 |
| EP | 351256 | * | 1/1990 |
| EP | 357466 | * | 3/1990 |
| EP | 0 652 428 A1 | | 5/1995 |
| EP | 1 069 423 A2 | | 1/2001 |
| WO | 89/04961 | * | 6/1989 |
| WO | 99/60378 | * | 11/1999 |
| WO | 00/49385 | | 8/2000 |

OTHER PUBLICATIONS

Noriyuki Tatsumi et al., Sysmex Journal International, vol. 9, No. 1, pp. 8–20, (1999).

* cited by examiner

*Primary Examiner*—Maureen M. Wallenhorst
(74) *Attorney, Agent, or Firm*—Birch, Stewart, Kolasch & Birch, LLP

(57) ABSTRACT

A blood cell detector includes an orifice section having a single orifice, a first supplying section for supplying a first blood specimen into the orifice section, a second supplying section for supplying a second blood specimen into the orifice section, and first and second electrodes provided on opposite sides of the orifice for detecting a change in impedance of each of the first and second blood specimens when the first and second blood specimens are selectively caused to pass through the orifice.

21 Claims, 8 Drawing Sheets

BLOOD CELL DETECTOR, BLOOD ANALYZER AND BLOOD ANALYZING METHOD USING THE DETECTOR

CROSS-REFERENCE TO RELATED APPLICATION

This application is related to Japanese Patent Application No. 2000-282458 filed in Sep. 18, 2000 whose priority is claimed under 35 USC §119, the disclosure of which is incorporated by reference in its entirety.

BACKGROUND OF THE INVENTION

1. Field of the Invention

The present invention relates to a detector for blood analysis and to a blood analyzer and a blood analyzing method. More particularly, the invention relates to a detector for analyzing white blood cells and red blood cells in a blood sample by an electric resistance method and to a blood analyzer for determination of the numbers and particle size distributions of the white blood cells and the red blood cells.

2. Description of the Related Art

In a conventional blood analyzer of electric resistance type having a flow circuit as shown in FIG. 1, white blood cells and red blood cells are analyzed in the following manner. The flow circuit includes a plurality of fluid devices such as values and pumps which make a network using tubes and nipples.

(1) A negative pressure is applied to a drain chamber 30 with valves V6, V7, V13 being open to discharge residual liquid from a mixing chamber 12, a white blood cell detector 10 and a red blood cell detector 11.

(2) A quantitative sampling pump 3 is driven for suction with a valve V1 being open to suck a predetermined amount of a blood sample into a pipette 1 from a sample container 2.

(3) With valves V2, V8 being open, a valve V5 is switched for communication between an outlet P1 and an inlet P2, and a negative pressure is applied to the drain chamber 30 to suck a diluent into the white blood cell detector 10 from a diluent supplying section 7 for cleaning the white blood cell detector 10. Similarly, with valves V3, V9 being open, the valve V5 is switched for communication between the outlet P1 and the inlet P3, and a negative pressure is applied to the drain chamber 30 for cleaning the red blood cell detector 11.

(4) A diluent pump 4 is driven for suction with the valve V8 being open to suck the diluent into a flow circuit from the diluent supplying section 7. Then, the diluent pump 4 is driven for pressurization with the valve V4 being open and with a valve V8 being closed to inject a predetermined amount of the diluent into the mixing chamber 12. Similarly, the dilution pump 4 is driven for suction with the valve V8 being open and with the valve V4 being closed to suck the diluent into the flow circuit from the diluent supplying section 7. Then, the diluent pump 4 is driven for pressurization with a valve V12 being open and with the valves V8, V4 being closed to inject a predetermined amount of the diluent into the red blood cell detector 11.

(5) The pipette 1 is moved to the mixing chamber 12 by a pipette driver (not shown). Then, the blood sample sucked into the pipette from the sample container 2 in Step (2) is discharged into the mixing chamber 12 by driving the quantitative sampling pump 3 for pressurization with the valve V1 being open. Thus, a blood specimen is prepared in the mixing chamber 12 through first-stage dilution of the blood sample.

(6) The pipette 1 is moved to the mixing chamber 12 by the pipette driver (not shown), and a diluent pump 5 is driven for suction with the valves V1, V45 being open to suck a predetermined amount of the blood specimen obtained through the first-stage dilution into the pipette from the mixing chamber 12. Then, the pipette 1 is moved to the white blood cell detector 10, and the diluent pump 5 is driven for pressurization with the valves V1, V45 being open to discharge the blood specimen into the white blood cell detector 10 from the pipette. This blood specimen is employed for the analysis of the white blood cells.

(7) As in Step (6), the pipette 1 is moved to the mixing chamber 12 by the pipette driver (not shown), and a predetermined amount of the blood specimen obtained through the first-stage dilution is sucked into the pipette from the mixing chamber 12. Then, the pipette 1 is moved to the red blood cell detector 11 by the pipette driver (not shown), and a predetermined amount of the blood specimen obtained through the first-stage dilution is discharged into the red blood cell chamber 11. Thus, a blood specimen is prepared in the red blood cell detector 11 through second-stage dilution. The blood specimen thus prepared in the red blood cell detector 11 is employed for the analysis of the red blood cells.

(8) A valve V10 is switched for communication between an outlet P4 and an inlet P6, and a hemolyzation agent pump 6 is driven for suction to introduce a hemolyzation agent into the flow circuit from a hemolyzation agent supplying section 8. Then, the valve V10 is switched to open the outlet P4 and the inlet P5, and the hemolyzation agent pump 6 is driven for pressurization to inject the hemolyzation agent into the white blood cell detector 10. After a lapse of a predetermined period, hemolyzation is completed in the white blood cell specimen retained in the white blood cell detector 10.

(9) The valve V5 is switched for communication between the outlet P1 and the inlet P2, and a negative pressure is applied to the discharge chamber 30 to suck the white blood cell specimen from the white blood cell detector 10 through an orifice 20. A change in impedance occurring when the white blood cell specimen passes through the orifice 20 is detected by electrodes 13, 14 for determination of the number and particle size distribution of the white blood cells. Similarly, the valve V5 is switched to open the outlet P1 and the inlet P3 to suck the red blood cell specimen from the red blood cell detector 11 through an orifice 21. A change in impedance occurring when the red blood cell specimen passes through the orifice 21 is detected by electrodes 15, 16 for determination of the number and particle size distribution of the red blood cells.

(10) The diluent pump 4 is driven for suction with the valve V8 being open to suck the diluent into the flow circuit from the diluent supplying section 7. Then, the diluent pump 4 is driven for pressurization with the valves V4, V11, V12 being open and with the valve V8 being closed to inject the diluent into the mixing chamber 12, the white blood cell detector 10 and the red blood cell detector 11.

(11) The quantitative sampling pump 3 is driven for suction with a valve V43 being open to suck the diluent into the flow circuit from a diluent supplying section 7. Then, the quantitative sampling pump 3 is driven for pressurization with the valve V1 being open and with the valve V43 being closed to clean a flow path extending from the quantitative sampling pump 3 to the pipette 1. At this time, the diluent flows out of a tip of the pipette 1, and is sucked into the drain chamber 30 in a manner as described in Step (12). On the other hand, the diluent pump 4 is driven for suction with the valve V8 being open to suck the diluent into the flow circuit from the diluent supplying section 7. Then, the diluent pump 4 is driven for pressurization with a valve V40 being open and with the valve V8 being closed to supply the diluent into a cleaning spitz 17. At this time, the diluent flows out of an outlet P10. Thus, the outer periphery of the pipette 1 is cleaned. Then, the diluent is sucked into the drain chamber 30 in the manner described in Step (12). The cleaning spitz 17 has a pipette receptor 27 into which the pipette 1 is inserted. A diluent inlet port 28 for supplying the diluent and a diluent suction port 29 for sucking the diluent are provided in a side wall of the pipette receptor 27.

(12) The cleaning spitz 17 is vertically moved along the pipette 1 by a cleaning spitz driver (not shown). A negative pressure is applied to the drain chamber 30 with a valve V41 being open, whereby the diluent flowing out of the pipette 1 and the outlet P10 in Step (11) is sucked into the drain chamber 30 through the inlet P11. Thus, the inside and outer periphery of the pipette 1 are cleaned.

(13) By performing Steps (1) to (12), the analysis of the blood sample is completed to be ready for the analysis of the next blood sample.

The orifices 20, 21 are each generally formed in a disk of artificial ruby, because they are required to be highly resistant to breakage and chemical agents and to have a high dimensional accuracy. As a material for the electrodes 13, 14, 15, 16 for the detection of the changes in impedance, platinum is employed which is highly resistant to chemical agents. Thus, the materials for the orifices and the electrodes are very expensive, increasing the costs of the conventional blood analyzer in which these components are provided in the white blood cell detector and the red blood cell detector. Since the white blood cell detector and the red blood cell detector are separately provided, the diluent pumps for supplying the diluent and the valves for switching the flow paths should be provided for each of the white blood cell detector and the red blood cell detector. This increases the complexity, size and costs of the analyzer.

SUMMARY OF THE INVENTION

In view of the foregoing, the present invention is directed to a detector which can singly achieve easy and accurate analysis of white blood cells and red blood cells. The present invention is further directed to simplification, size reduction and cost reduction of a blood analyzer.

In accordance with the present invention, there is provided a blood cell detector which comprises an orifice section having a single orifice, a first supplying section for supplying a first blood specimen into the orifice section, a second supplying section for supplying a second blood specimen into the orifice section, and first and second electrodes provided on opposite sides of the orifice for detecting a change in impedance of each of the first and second blood specimens when the first and second blood specimens are selectively caused to pass through the orifice.

DESCRIPTION OF THE PREFERRED EMBODIMENTS

Figure 1:
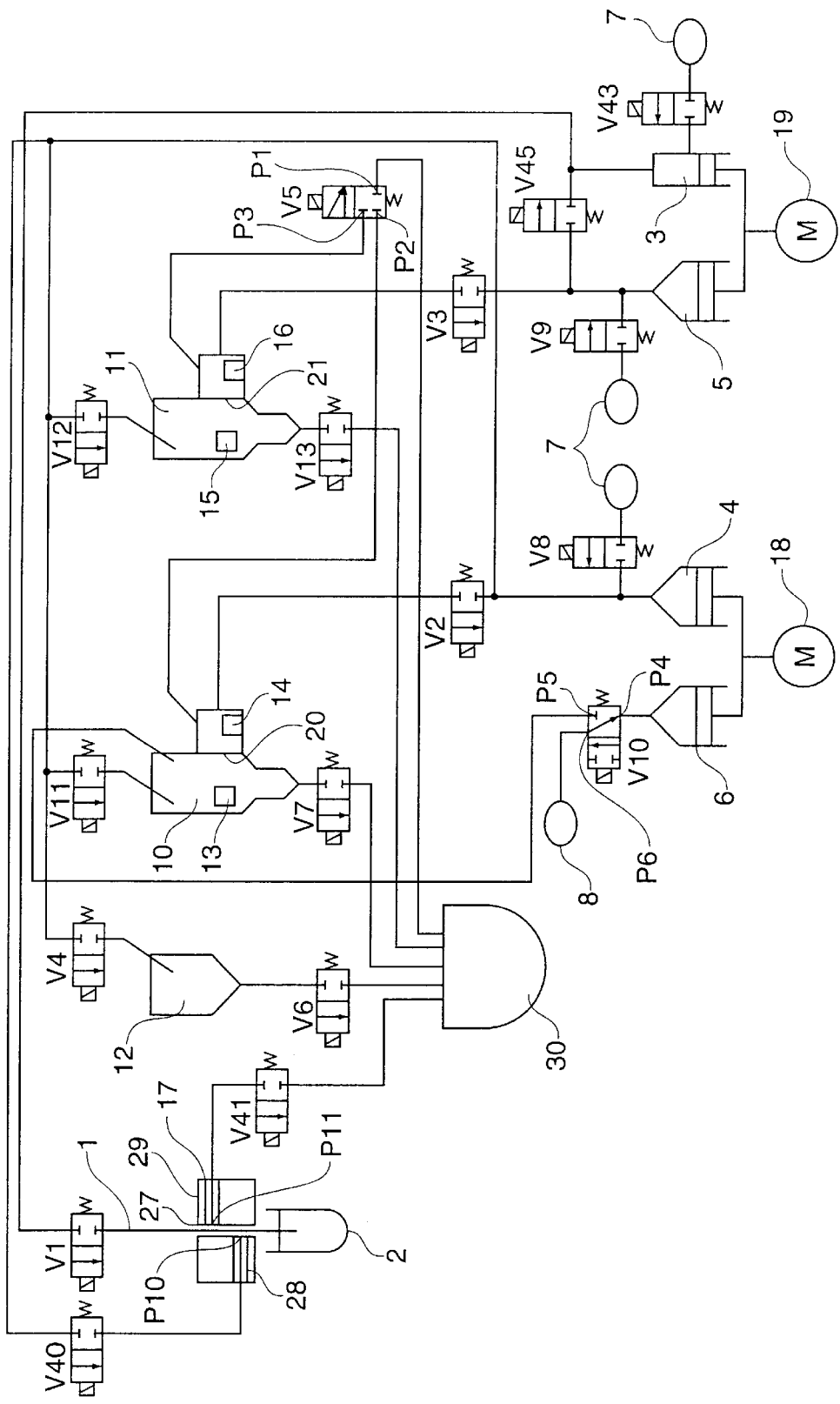
FIG. 1 is a flow circuit diagram of a conventional blood analyzer.

The blood cell detector according to the present invention comprises an orifice section having a single orifice, a first supplying section for supplying a first blood specimen into the orifice section, a second supplying section for supplying a second blood specimen into the orifice section, and first and second electrodes provided on opposite sides of the orifice for detecting a change in impedance of each of the first and second blood specimens when the first and second blood specimens are selectively caused to pass through the orifice.

The first and second blood specimens may be caused to pass through the orifice in the same direction or in opposite directions.

The first blood specimen may be a specimen for analysis of white blood cells, and the second blood specimen may be a specimen for analysis of red blood cells.

The first supplying section may include a container pervious to light for retaining a specimen for analysis of hemoglobin, a light source for applying light to the container, and a light receiving section for receiving light transmitted through the container.

The second supplying section may include sheath flow means for causing the red blood cell specimen to be enclosed in a sheath liquid to pass through the orifice.

The sheath flow means may include a nozzle for ejecting the red blood cell specimen into the orifice, and a sheath liquid supplying section for supplying the sheath liquid in which the red blood cell specimen is enclosed to pass through the orifice.

The first and second supplying sections may include first and second blood specimen containers, respectively.

The first supplying section may include a blood specimen container for retaining the first blood specimen, and the second supplying section may include a nozzle for ejecting the second blood specimen into the orifice, and a sheath liquid supplying section for supplying a sheath liquid in which the ejected second blood specimen is enclosed to pass through the orifice.

In accordance with another aspect of the present invention, there is provided a blood analyzer having the aforesaid blood cell detector.

In the present invention, an electric resistance method is employed for detection of blood cells. The electric resistance method has such drawbacks that there are variations in detection signal depending on a position in the orifice through which each particle passes, that a plurality of particles passing through the orifice in a close positional relation are counted as a single particle, and that particles having passed through the orifice are liable to stay in the vicinity of the orifice to cause noises. To cope with these drawbacks, a sheath flow method is advantageously employed. The sheath flow method herein means a method such that a specimen is fed into the orifice while being enclosed in a sheath liquid. In this method, particles in the specimen are prevented from being brought into a close positional relation, and allowed to pass through the center of the orifice. In the present invention, therefore, a nozzle is preferably provided for allowing the red blood cell specimen to be enclosed in the sheath liquid to be fed into the orifice. This drastically improves the accuracy of the analysis of the red blood cells and platelets. Further, a measuring factor for the red blood cell specimen can be reduced, thereby allowing for reduction in the consumption of a diluent and drastic reduction in the period required for the analysis.

Basic blood analysis items include the number of white blood cells (WBC), the number of red blood cells (RBC), the number of platelets (PLT), the amount of hemoglobin (HGB), and hematocrit (HCT). The hematocrit is determined by processing red blood cell detection signals. The inventive blood cell detector preferably further includes a hemoglobin specimen container for retaining a hemoglobin specimen for determination of the hemoglobin amount. With this arrangement, the blood analyzer having the inventive blood cell detector is capable of determining all the basic blood analysis items.

Among the white blood cells, the red blood cells and the platelets, the red blood cells and the platelets are present in concentrations of about $4,000,000/\mu l$ and about $200,000/\mu l$, respectively, in a normal blood sample and, hence, differ in concentration by an order of magnitude. Further, the red blood cells and the platelets differ in size and, therefore, can simultaneously be analyzed by employing the same blood specimen. On the other hand, the white blood cells are present in a concentration of about $5,000/\mu l$ in a normal blood sample and, hence, are smaller in concentration by three orders of magnitude than the red blood cells, but similar in size to the red blood cells. Therefore, it is impossible to simultaneously analyze the red blood cells and the white blood cells by employing the same blood specimen. For the analysis of the white blood cells, a hemolyzed blood sample is employed. An hemolyzation agent for hemolyzation for the white blood cell analysis may also be employed for hemolyzation for the hemoglobin analysis, depending on its composition.

In the blood cell analysis, the blood cells are preferably allowed to pass through the orifice at predetermined intervals for higher accuracy. Therefore, the white blood cells and the red blood cells which are different in concentration are separately analyzed by diluting a blood sample by different dilution factors. Since the platelets and the red blood cells in blood are two to three orders of magnitude greater in concentration than the white blood cells, the dilution factor for the red blood cell specimen should correspondingly be increased as compared with the dilution factor for the white blood cell specimen. Therefore, it is a conventional practice to dilute the blood sample, for example, 25,000 times for the red blood cell specimen and 500 times for the white blood cell specimen and supply the red blood cell specimen and the white blood cell specimen to the corresponding detectors. Where the sheath flow method is employed, on the other hand, the dilution factor for the red blood cell specimen can be reduced to about 750, while the dilution factor for the white blood cell specimen is 500.

As described above, the blood sample to be analyzed is diluted by different dilution factors for the red blood cell specimen and for the white blood cell specimen. Where the blood sample is diluted with a diluent by a high dilution factor, e.g., by a factor of 25,000, at one time, the ratio of the amount of the blood sample to the amount of the diluent is so small that an error in the amount of the blood sample significantly influences the analysis. Therefore, it is preferred to prepare the red blood cell specimen through two-stage dilution, and to prepare the white blood cell specimen through one-stage dilution.

With reference to the attached drawings, the present invention will hereinafter be described in detail by way of embodiments thereof. It should be understood that the invention be not limited to the embodiments.

Embodiment 1

Figure 2:
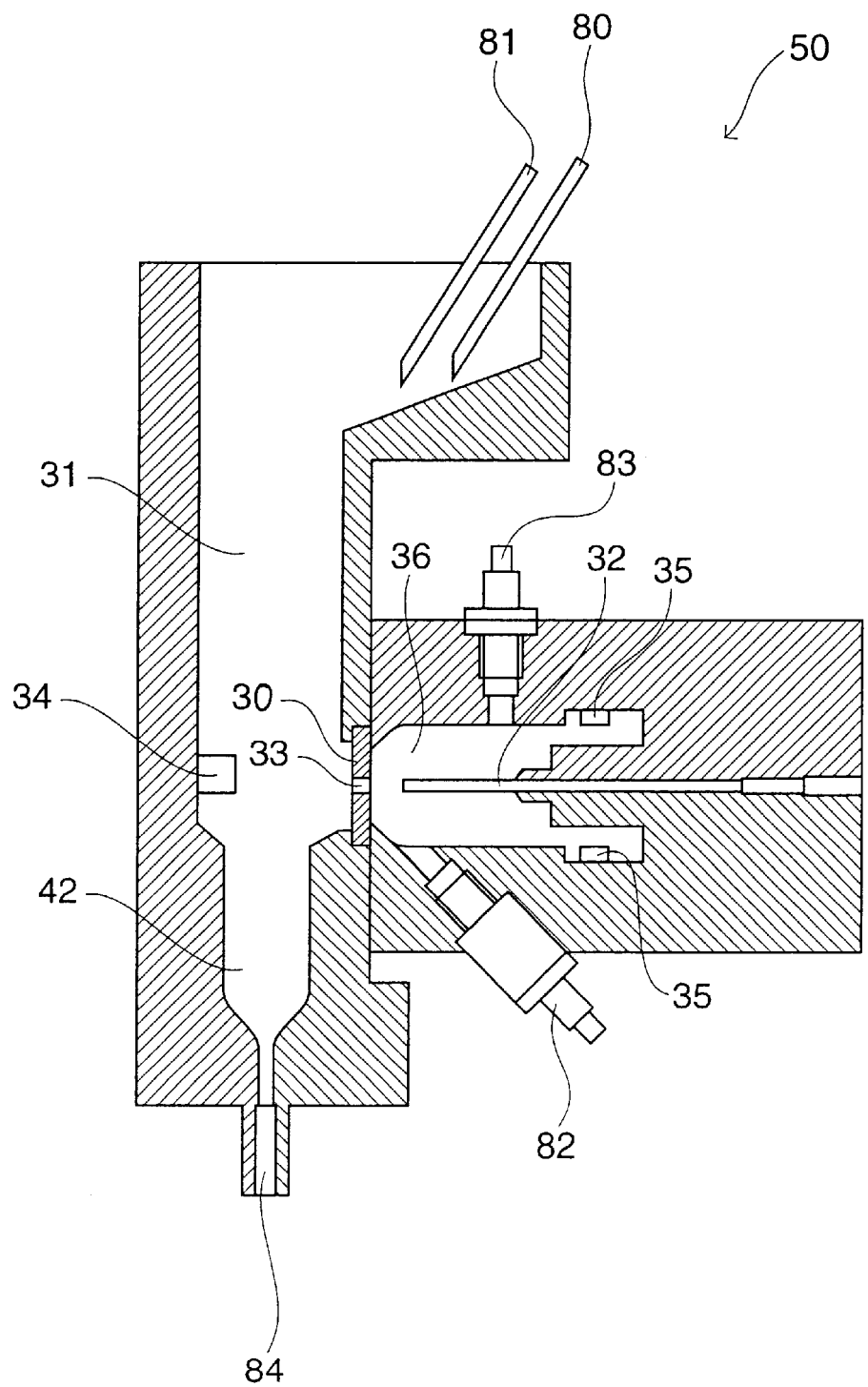
FIG. 2 is a sectional view illustrating a white blood cell and red blood cell detector according to Embodiment 1.
Figure 3:
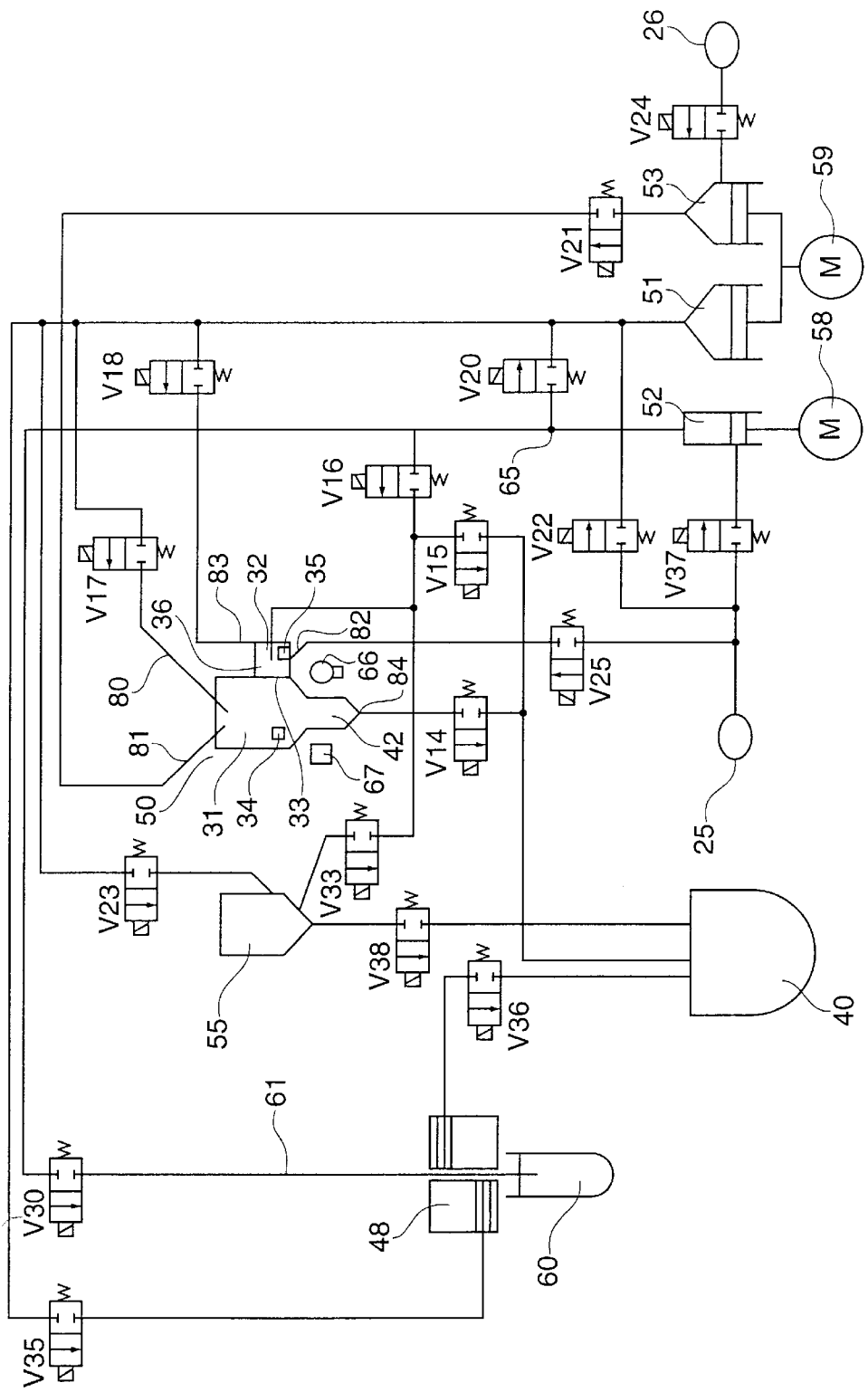
FIG. 3 is a flow circuit diagram of a blood analyzer according to Embodiment 1.

FIG. 2 is a sectional view illustrating a white blood cell and red blood cell detector to be employed in Embodiment 1, and FIG. 3 shows a flow circuit of a blood analyzer according to Embodiment 1. The flow circuit includes a plurality of fluid devices which make a network using tubes and nipples.

As shown in FIG. 2, the white blood cell and red blood cell detector 50 includes a first liquid container 31, a second liquid container 36, a third liquid container 42, a disk 30 having an orifice 33, a jet nozzle 32, and electrodes 34, 35 (a negative electrode 34 and a positive electrode 35) for detecting a change in impedance. The orifice 33 has a diameter that allows for passage of a white blood cell and a red blood cell. Changes in impedance detected by the electrodes 34, 35 when a blood cell passes through the center of the orifice 33 and when the blood cell passes through a portion of the orifice other than the center thereof differ from each other. This reduces the accuracy of the analysis. That is, if the diameter of the orifice 33 is too great with respect to the diameter of the blood cell, the blood cell does not pass through a constant position in the orifice 33, resulting in reduction in the accuracy of the analysis. In this connection, the diameter of the orifice 33 is herein set to $50 \mu m$–$100 \mu m$. Preferably, the diameter is $80 \mu m$. In this embodiment, the first liquid container 31 and the third liquid container 42 are combined together, and the third liquid container 42 is a rectangular column of a transparent polysulfone resin pervious to light. However, the material for the third liquid container is not limited to the polysulfone resin, but may be glass. The shape of the third liquid container is not limited to a rectangular shape, but may be a cylindrical shape or a combination of a rectangular shape and a cylindrical shape. A diluent and a hemolyzation agent are respectively pumped into the first liquid container 31 via a diluent injection nozzle 80 and a hemolyzation agent injection nozzle 81 by a diluent pump 51 and a hemolyzation agent pump 53 shown in FIG. 3. The second liquid container 36 is provided with nipples 82, 32 for connection to an external flow circuit. Liquid within the first liquid container 31 and the third liquid container 42 is discharged from a drain nipple 84.

A mixing chamber 55 shown in FIG. 3 and the first liquid container 31 each have an open top, through which a blood sample and the like are injected from a pipette 61.

The diluent pump 51, a quantitative sampling pump 52 and the hemolyzation agent pump 53 shown in FIG. 3 are driven by stepping motors 58, 59.

In FIG. 3, reference characters V14 to V18, V20 to V24, V30, V33, V35 to V38 denote electromagnetic valves. It is herein assumed that these valves are normally closed.

Figure 8:
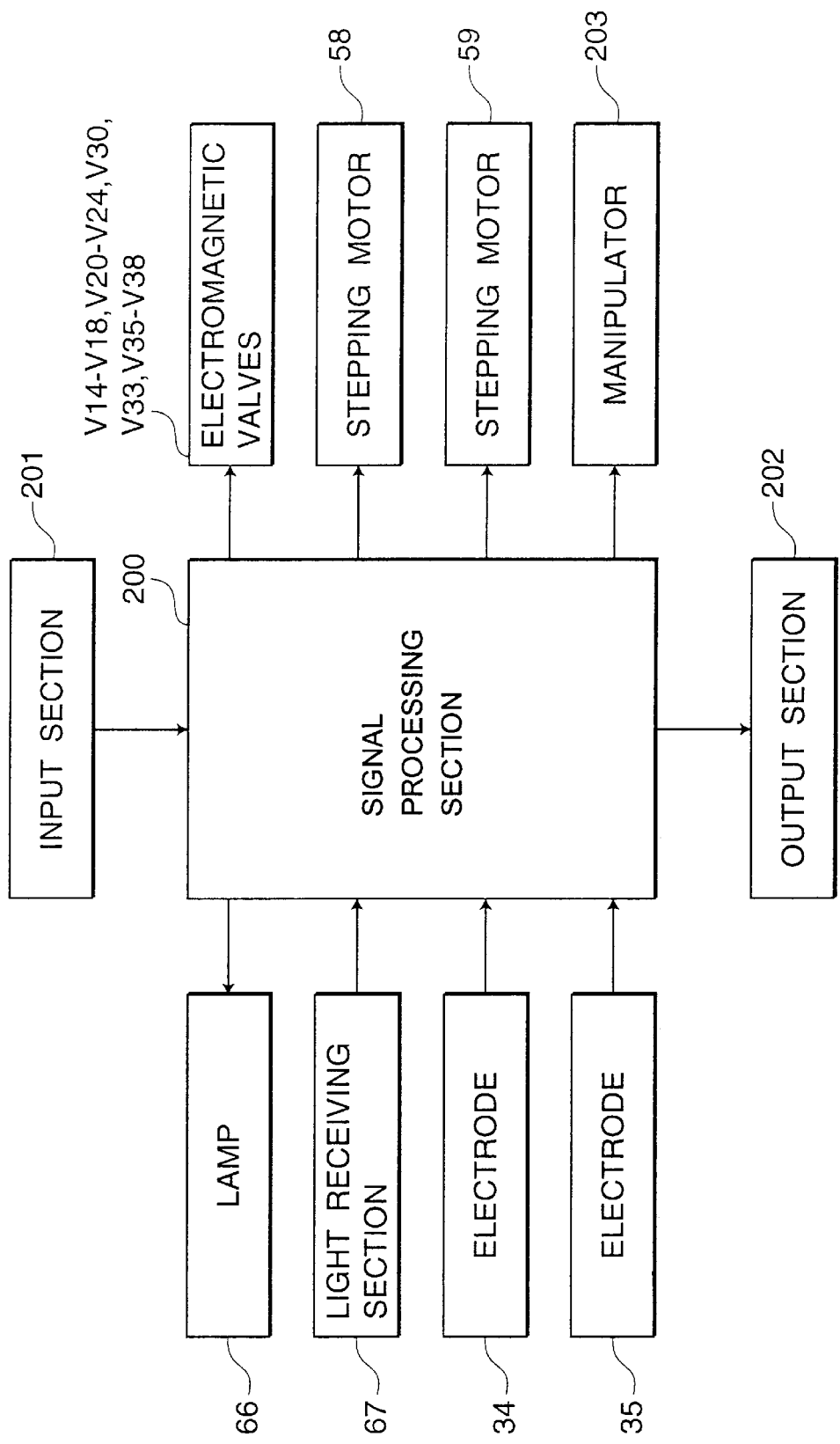
FIG. 8 is an electric circuit diagram of the blood analyzer according to Embodiment 1.

FIG. 8 is an electric circuit diagram of the blood analyzer according to Embodiment 1.

As shown in FIG. 8, a signal processing section 200 receives a signal from an input section 201 for presetting various processing conditions of the signal processing section 200 and outputs driving signals to the electromagnetic values V14–V18, V20–V24, V30, V33 and V35–V38, the stepping motors 58, 59 and a manipulator 203 for manipulating the pipette 61. The signal processing section 200 also drives a lamp 66 and receives signals from a light receiving section 67 (see, FIG. 3) and the electrodes 34, 35. The signal processing section 200 processes the signal from the electrodes 34, 35 for determination of WBC, RBC, PLT and HCT and also processes the signal from the light receiving section 67 for determination of the hemoglobin amount (HGB). A result of the determination is output from an output section 202.

The signal processing section 200 includes a microcomputer having a CPU, a ROM and a RAM and driving circuits for driving the electromagnetic values V14–V18, V20–V24, V30, V33, and V35–V38, the stepping motors 58, 59, the manipulator 203 and the lump 66. The lump 66 is a light emitting diode and the light receiving section includes a photo diode. The manipulator 203 includes stepping motors for moving the pipette 61 vertically and horizontally.

Sequence of White Blood Cell Analysis

The analysis of white blood cells is carried out in the following sequence.

(1) The quantitative sampling pump 52 is driven for suction with the valve V30 being open to suck a predetermined amount of a blood sample into the pipette 61 from a sample container 60.

(2) A negative pressure is applied to a drain chamber 40 with the valves V14, V38 being open to discharge residual liquid from the first liquid container 31 and the mixing chamber 55 into the drain chamber 40.

(3) The diluent pump 51 is driven for suction with the valve V22 being open to suck the diluent into the flow circuit from a diluent supplying section 25. Then, the diluent pump 51 is driven for pressurization with the valve V23 being open and with the valve V22 being closed to inject a predetermined amount of the diluent into the mixing chamber 55.

(4) The pipette 61 is moved to the mixing chamber 55 by a pipette driver (not shown), and the blood sample previously sucked into the pipette is discharged into the mixing chamber 55. Thus, a blood specimen is prepared in the mixing chamber 55 through first-stage dilution.

(5) The diluent pump 51 is driven for suction with the valve V22 being open to suck the diluent into the flow circuit from the diluent supplying section 25. Then, the diluent pump 51 is driven for pressurization with the valve V17 being open and with the valve V22 being closed to inject a predetermined amount of the diluent into the first liquid container 31. At the same time, the hemolyzation agent pump 53 is driven for suction with the valve V24 being open to suck the hemolyzation agent into the flow circuit from a hemolyzation agent supplying section 26. Then, the hemolyzation agent pump 53 is driven for pressurization with the valve V21 being open and with the valve V24 being closed to inject a predetermined amount of the hemolyzation agent into the first liquid container 31.

(6) A predetermined amount of the diluted blood specimen prepared in Step (4) (a half of the specimen in the mixing chamber) is sucked into the pipette 61 from the mixing chamber 55. Then, the pipette 61 is moved to the first liquid container 31 by the pipette driver (not shown), and the diluted blood specimen sucked into the pipette is discharged into the first liquid container 31. Thus, a white blood cell specimen is prepared through second-stage dilution. By controlling the amount of the diluent to be injected into the first liquid container 31, the white blood cell specimen is allowed to have a greater concentration than a red blood cell specimen to be described later. The preparation of the white blood cell specimen is not necessarily required to be achieved through two-stage dilution, but a white blood cell specimen prepared through one-stage dilution may be employed as it is. In this embodiment, the suction and injection amounts of the diluent are controlled so that the blood sample is diluted 500 times for the preparation of the white blood cell specimen. During a predetermined period, the white blood cell specimen is subjected to hemolyzation with the hemolyzation agent.

(7) A negative pressure is applied to the drain chamber 40 with the valves V15, V16, V18, V20, V25 being open, whereby the diluent is sucked into the flow circuit from the diluent supplying section 25 and discharged into the drain chamber 40 via the nipples 82, 83 and the valves V18, V20, V16, V15. Thus, the second liquid container 36 is filled with the diluent, so that dirt and bubbles can be removed from the inside of the second liquid container 36. Therefore, an error in the analysis of the white blood cells can be prevented which may otherwise occur due to the dirt and the bubbles.

(8) A negative pressure is applied to the drain chamber 40 with the valve V25 being closed and with the valves V15, V16, V18, V20 being open, whereby the white blood cell specimen is sucked from the first liquid container 31 through the orifice 33, the second liquid container 36, the nipple 83 and the valves V18, V20, V16, V15. A change in impedance occurring at this time is detected by the electrodes 34, 35 for determination of the number and particle size distribution of the white blood cells.

Sequence of Red Blood Cell Analysis

The analysis of red blood cells is carried out in the following sequence.

(1) A negative pressure is applied to the drain chamber 40 with the valves V15, V16, V18, V20, V25 being open, whereby the diluent is sucked into the flow circuit from the diluent supplying section 25 and discharged into the drain chamber 40 through the nipples 82, 83 and the valves V18, V20, V16, V15. Thus, the second liquid container 36 is filled with the diluent. Further, the white blood cell specimen remaining after the white blood cell analysis is removed from the second liquid container 36 and, at the same time, bubbles are removed from the inside of the second liquid container 36.

(2) A negative pressure is applied to the drain chamber 40 with the valve V14 being open to discharge residual liquid from the first liquid container 31 into the drain chamber 40.

(3) The diluent pump 51 is driven for suction with the valve V22 being open to suck the diluent into the flow circuit from the diluent supplying section 25. Then, the diluent pump 51 is driven for pressurization with the valve 17 being open and with the valve V22 being closed to inject a predetermined amount of the diluent into the first liquid container 31.

(4) The diluent pump 51 is driven for suction with the valve V22 being open to suck the diluent into the flow circuit from the diluent supplying section 25. Then, the diluent pump 51 is driven for pressurization with the valves V33, V16, V20 being open and with the valve V22 being closed to inject a predetermined amount of the diluent into the mixing chamber 55 through the valves V20, V16, V33. Since the blood specimen prepared for the white blood cell analysis remains in the mixing chamber 55, a red blood cell specimen is prepared from the white blood cell specimen through second-stage dilution. In this embodiment, the suction and injection amounts of the diluent are controlled so that the blood sample is diluted 750 times for the preparation of the red blood cell specimen.

(5) The diluent pump 51 is driven for suction with the valves V33, V16, V20 being open and with the valve V22 being closed to suck the red blood cell specimen into a flow path 65 from the mixing chamber 55.

(6) The quantitative sampling pump 52 is driven for pressurization with the valves V33, V20 being closed and with the valve V16 being kept open to inject the red blood cell specimen into the first liquid container 31 through the orifice 33 from the jet nozzle 32 via the valve V16.

(7) Simultaneously with Step (6), the diluent pump 51 is driven for suction with the valve V22 being open to suck the diluent into the flow circuit from the diluent supplying section 25. Then, the diluent pump 51 is driven for pressurization with the valve V18 being open and with the valve V22 being closed, whereby the diluent is supplied into the second liquid container 36 via the valve V18 and the nipple 83 and then forced out of the second liquid container into the first liquid container 31 through the orifice 33. Thus, a sheath flow formed by enclosing the red blood cell specimen in the diluent passes through the orifice 33. This drastically improves the accuracy of the red blood cell analysis. A change in impedance occurring when the red blood cell specimen and the diluent pass through the orifice 33 is detected by the electrodes 34, 35 for determination of the numbers and particle size distributions of the red blood cells and the platelets.

Sequence of Detector Cleaning

The cleaning of the detector for the next blood analysis is carried out in the following sequence.

(1) A negative pressure is applied to the drain chamber 40 with the valve V14 being open to discharge residual liquid from the first liquid container 31 into the drain chamber 40.

(2) The diluent pump 51 is driven for suction with the valve V22 being open to suck the diluent into the flow circuit from the diluent supplying section 25. Then, the diluent pump 51 is driven for pressurization with the valve V17 being open and with the valve V22 being closed to inject a predetermined amount of the diluent into the first liquid container 31.

(3) A negative pressure is applied to the drain chamber 40 with the valves V15, V16, V18, V20, V25 being open, whereby the diluent is sucked into the flow circuit from the diluent supplying section 25 and discharged into the drain chamber 40 through the nipples 82, 83 and the valves V18, V20, V16, V15. Thus, the second liquid container 36 and its peripheral flow paths are cleaned and, upon completion of the cleaning, filled with the diluent.

(4) The quantitative sampling pump 52 is driven for suction with the valve V37 being open to suck the diluent into the flow circuit from the diluent supplying section 25. Then, the quantitative sampling pump 52 is driven for pressurization with the valve V30 being open and with the valve V37 being closed to clean a flow path extending from the quantitative sampling pump 52 to the pipette 61. At this time, the diluent flows out of a tip of the pipette 61, and sucked into the drain chamber 40 in a manner as described in Step (5). On the other hand, the diluent pump 51 is driven for suction with the valve V22 being open to suck the diluent into the flow circuit from the diluent supplying section 25. Then, the diluent pump 51 is driven for pressurization with the valve V35 being open and with the valve V22 being closed to supply the diluent into a cleaning spitz 48. The cleaning spitz 48 has the same construction as the cleaning spit 29 shown in FIG. 1, so that no explanation will be given thereto.

(5) The cleaning spitz 48 is moved along the pipette 61 by a cleaning spitz driver (not shown), and a negative pressure is applied to the drain chamber 40 with the valve V36 being open to suck the diluent used in Step (4) into the drain chamber 40. This operation is performed in substantially the same manner as in the prior art explained with reference to FIG. 1. Thus, the pipette 61 is cleaned.

Sequence of Hemoglobin Analysis

For the analysis of hemoglobin, the absorbance of a hemolyzed blood sample is measured. Where STROMATOLYSER(™) WH (available from Sysmex) is employed as the hemolyzation agent, the hemolyzation can effectively be carried out for the white blood cell analysis and for the hemoglobin analysis. The absorbance is first measured with the diluent retained in the third liquid container 42 for blank measurement, and then is measured with a hemoglobin specimen retained in the third liquid container 42 by the lamp 66 and the light receiving section 67. The hemoglobin amount is determined by calculating a difference between the measurements of the absorbance.

The analysis of the hemoglobin is carried out in the following sequence.

(1) When the detector 50 is cleaned, i.e., after completion of the red blood cell analysis, the absorbance (blank level) is measured with the diluent retained in the first liquid container 31 (Step (2) in the sequence of the detector cleaning) by the lamp 66 and the light receiving section 67.

(2) Immediately before Step (8) in the sequence of the white blood cell analysis, i.e., immediately before the negative pressure is applied to the drain chamber 40 with the valve V25 being closed and with the valves V15, V16, V18, V20 being open to suck the white blood cell specimen into the second liquid container 36 through the orifice 33 from the first liquid container 31, the absorbance is measured in the third liquid container 42 by the lamp 66 and the light receiving section 67.

(3) The hemoglobin amount is determined by calculating a difference between the measurements of the absorbance in a known manner.

Figure 7:
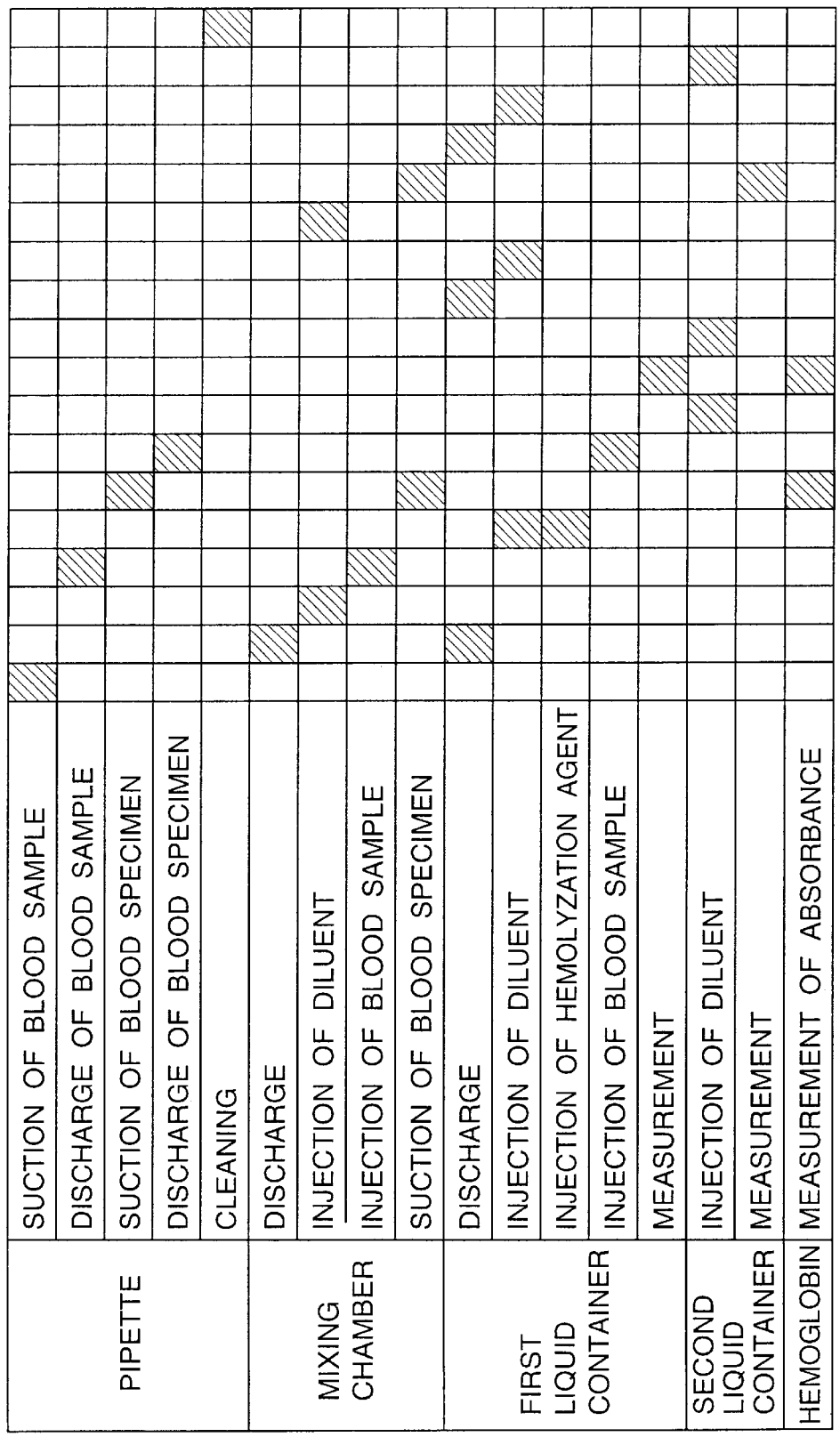
FIG. 7 is a timing chart for explaining operations to be performed by respective components of the blood analyzer according to Embodiment 1.

For easy understanding of the operation of the blood analyzer according to Embodiment 1, a timing chart is shown in FIG. 7 which illustrates operations to be performed in the respective components over time (in the order from the left side to the right side). Hatched portions in the timing chart indicate operating periods.

Embodiment 2

Figure 4:
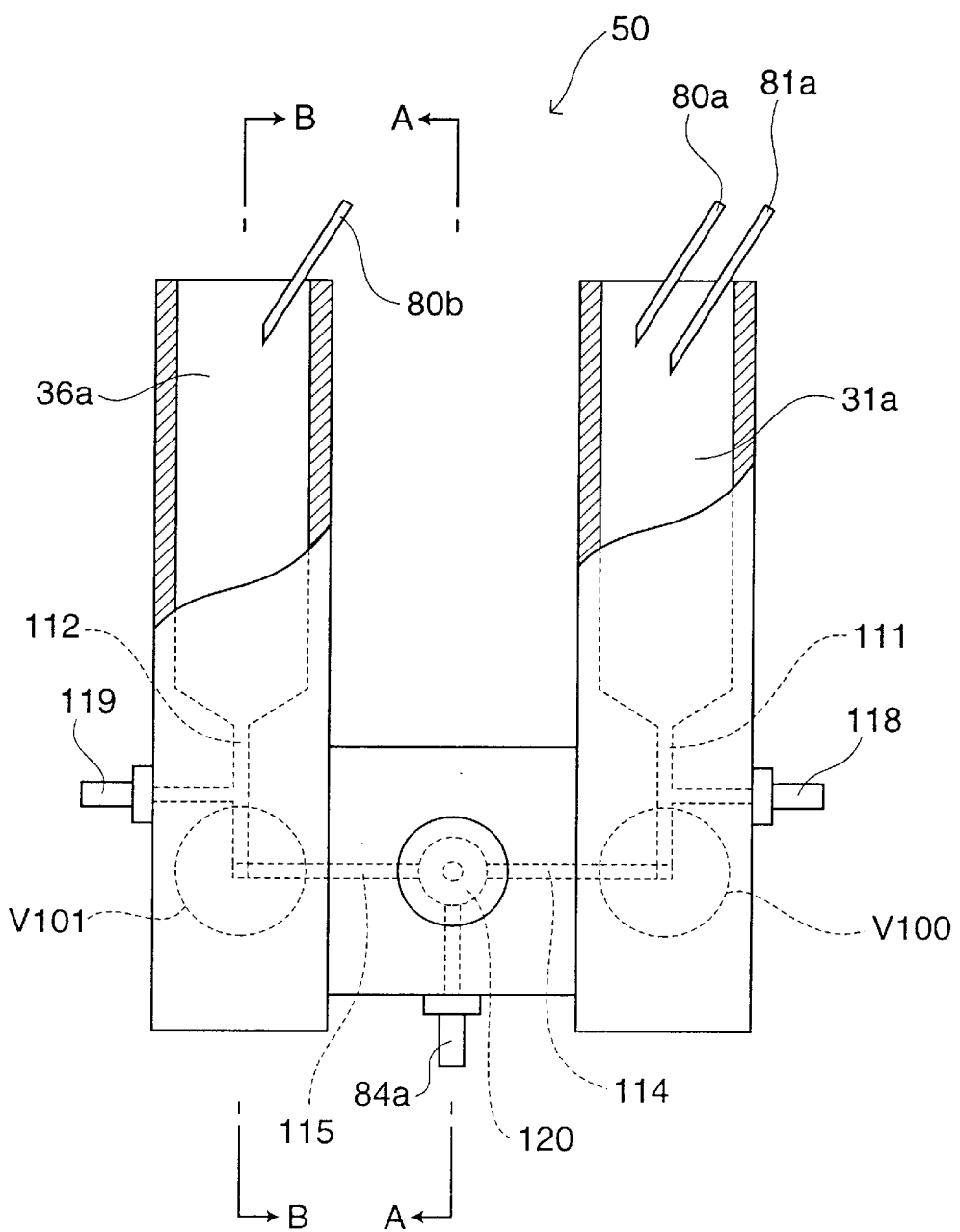
FIG. 4 is a front view illustrating a white blood cell and red blood cell detector according to Embodiment 2.
Figure 5:
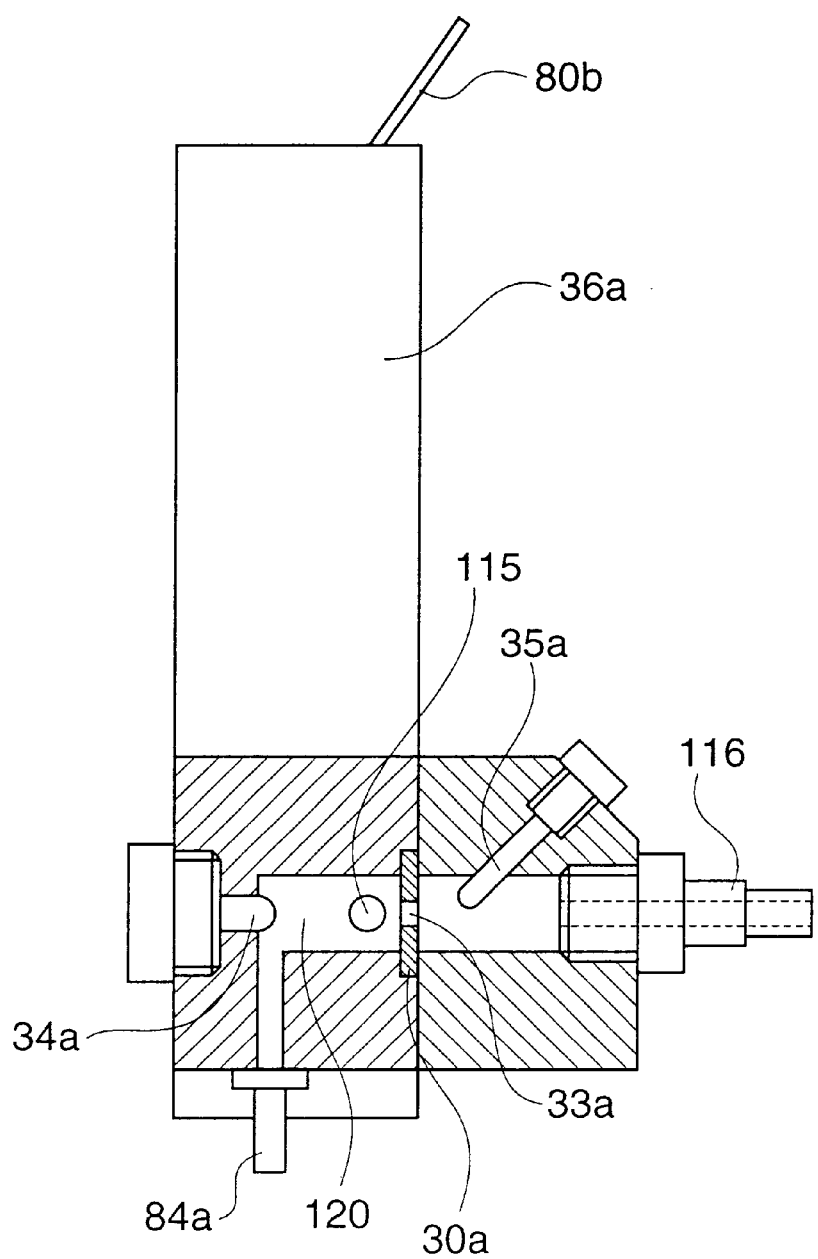
FIG. 5 is a sectional view as seen in the direction of arrows A—A in FIG. 4.

Although the detector according to Embodiment 1 is adapted to perform the analysis by causing the white blood cell specimen and the red blood cell specimen to pass through the orifice by suction and by pressurization, respectively, a detector according to this embodiment is adapted to perform the analysis by causing the white blood cell specimen and the red blood cell specimen to pass through the orifice by suction. An explanation will be given to Embodiment 2 with reference to FIGS. 4 to 6. FIG. 4 is a front view illustrating a white blood cell and red blood cell detector 50a according to Embodiment 2. FIG. 5 is a sectional view as seen in the direction of arrows A—A in FIG. 4, and FIG. 6 is a sectional view as seen in the direction of arrows B—B in FIG. 4.

Figure 6:
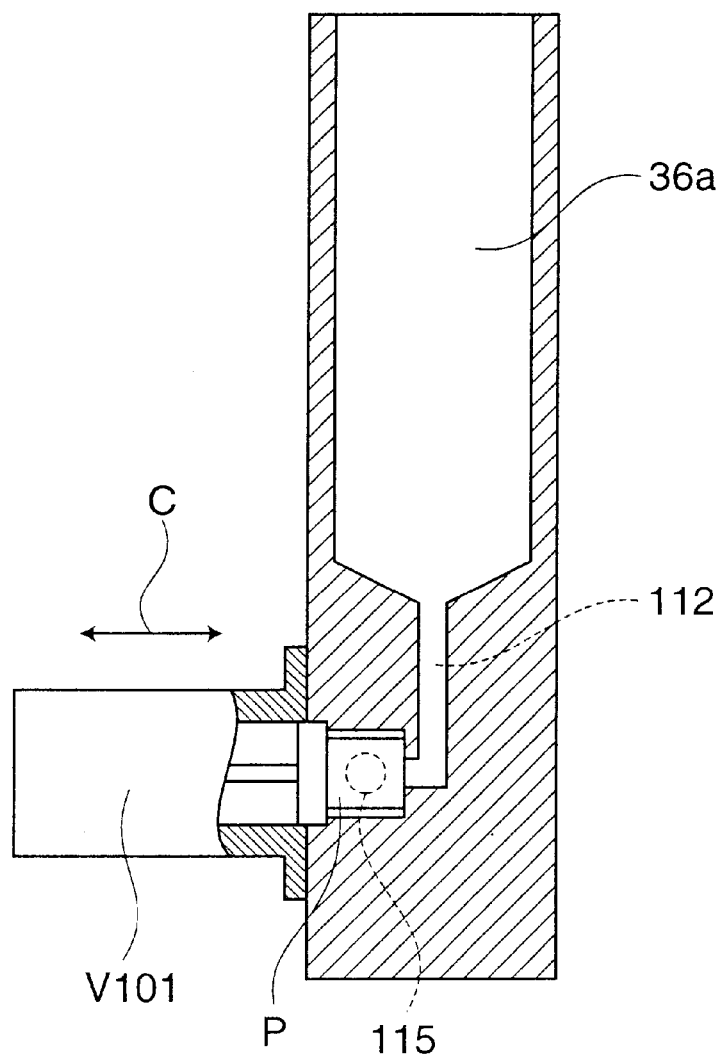
FIG. 6 is a sectional view as seen in the direction of arrows B—B in FIG. 4.

As shown in FIGS. 4 to 6, the white blood cell and red blood cell detector 50a includes a first liquid container 31a for retaining a white blood cell specimen, a second liquid container 36a for retaining a red blood cell specimen, a disk 30a having an orifice 33a, electrodes 34a, 35a (a negative electrode 34a and a positive electrode 35a) for detecting a change in impedance, and an electrode chamber 120 in which the electrode 34a is disposed. For the analysis of white blood cells, the white blood cell specimen is supplied from the first liquid container 31a through a flow path 114 and the electrode chamber 120, and caused to pass through the orifice 33a. For the analysis of red blood cells, the red blood cell specimen is supplied from the second liquid container 36a through a flow path 115 and the electrode chamber 120, and caused to pass through the orifice 33a.

The orifice 33a has a diameter of 80 μm as in Embodiment 1.

The first and second liquid containers 31a, 36a respectively have open tops, through which a diluent and a hemolyzation agent are injected therein from diluent injection nozzles 80a, 80b and a hemolyzation agent injection nozzle 81a. Further, a blood sample is injected from a pipette (not shown) through the open tops of the first and second liquid containers 31a, 36a.

The detector 50a further has nipples 84a, 116, 118, 119 for connection to an external flow circuit.

A valve V100 is switched to prevent or permit passage of the white blood cell specimen from a discharge path 111 of the first liquid container 31a to the flow path 114. Similarly, a valve V101 is switched to prevent or permit passage of the red blood cell specimen from a discharge path 112 of the second liquid container 36a to the flow path 115. The valves V100, V101 are switched to open or close the flow paths 114 and 115, respectively, by moving movable pieces P therein in the direction of an arrow C.

Next, an explanation will be given to the sequence of the analysis to be performed with the use of the white blood cell and red blood cell detector 50a according to Embodiment 2. Flow paths for the blood sample, the diluent, the hemolyzation agent and the like and the sequences of the preparation of the blood specimens are the same as in Embodiment 1, so that no explanation will be given thereto.

(1) With the valves V100, V101 being open, residual liquid is discharged from the first liquid container 31a and the second liquid container 36a in the same manner as in Step (1) of the sequence of the white blood cell analysis according to Embodiment 1.

(2) After the valves V100, V101 are closed, the white blood cell specimen is prepared in the first liquid container 31a in the same manner as in Steps (2) to (6) of the sequence of the white blood cell analysis according to Embodiment 1. At this time, the amounts of the blood sample and the diluent are controlled so that the blood sample is diluted 500 times for the preparation of the white blood cell specimen.

(3) With the valve V100 being open, the white blood cell specimen is sucked through the flow paths 111, 114, the orifice 33a and the nipple 116. A change in impedance occurring when the white blood cell specimen passes through the orifice 33a is detected by the electrodes 34a, 35a for determination of the number and particle size distribution of the white blood cells.

(4) The diluent is supplied from the diluent injection nozzle 80a to be filled in the first liquid container 31a, and then sucked in the same manner as in Step (3). Thus, the first liquid container 31a, the electrode chamber 120 and the like are cleaned.

(5) After the valves V101, V100 are closed, the red blood cell specimen is prepared in the second liquid container 36a in substantially the same manner as in Steps (2) to (6) of the sequence of the white blood cell analysis according to Embodiment 1. However, the hemolyzation agent is not injected into the second liquid container 36a at this time. The amounts of the blood sample and the diluent are controlled so that the blood sample is diluted 25,000 times for the preparation of the red blood cell specimen.

(6) With the valve V101 being open, the red blood cell specimen is sucked through the flow paths 112, 115, the orifice 33a and the nipple 116. A change in impedance occurring when the red blood cell specimen passes through the orifice 33a is detected by the electrodes 34a, 35a for determination of the number and particle size distribution of the red blood cells.

(7) The diluent is supplied from the diluent injection nozzle 80b to be filled in the second liquid container 36a, and then sucked in the same manner as in Step (6). Thus, the second liquid container 36a, the electrode chamber 120 and the like are cleaned.

(8) After the valves V100, V101 are closed, the diluent is injected into the first and second liquid container 31a, 36a through the diluent injection nozzles 80a, 80b to be ready for the next blood analysis.

Where the white blood cell and red blood cell detector 50a according to Embodiment 2 has a hemoglobin specimen retaining section provided in the first liquid container 31a thereof, a lamp and a light receiving section, the hemoglobin analysis can be performed.

Where the detector is adapted to intermittently inject air for a predetermined period into the specimens in the first and second liquid containers 31a, 36a through the nipples 118, 119, the specimens can be agitated. Thus, variations in the concentrations of the specimens in the containers can be eliminated for improvement of the accuracy of the analysis.

In accordance with the present invention, white blood cells and red blood cells in a blood sample can easily and accurately be analyzed with the use of a single detector. Since the number of diluent pumps, the number of valves and the number of electrodes can be reduced, a less expensive blood analyzer can be provided which has a simplified construction and a reduced size.

What is claimed is:

1. A blood cell detector comprising:
   an orifice section having a single orifice;
   a first supplying section connected to the orifice section for supplying a first blood specimen into the orifice section;
   a second supplying section connected to the orifice section for supplying a second blood specimen into the orifice section; and
   first and second electrodes provided on opposite sides of the orifice for detecting a change in impedance of each of the first and second blood specimens when the first and second blood specimens are selectively caused to pass through the orifice
   wherein the first and second supplying sections cause the first and second blood specimens to pass through the orifice in opposite directions.

2. A blood cell detector as set forth in claim 1, wherein the first blood specimen is a specimen for analysis of white blood cells, and the second blood specimen is a specimen for analysis of red blood cells.

3. A blood cell detector as set forth in claim 2, wherein the second supplying section includes sheath flow means for causing the red blood cell specimen to be enclosed in a sheath liquid to pass through the orifice.

4. A blood cell detector as set forth in claim 3, wherein the sheath flow means includes a nozzle for ejecting the red blood cell specimen into the orifice, and a sheath liquid supplying section for supplying the sheath liquid in which the red blood cell specimen is enclosed to pass through the orifice.

5. A blood cell detector as set forth in claim 3, wherein the sheath liquid is a diluent for preparing at least one of the first and second blood specimen.

6. A blood cell detector as set forth in claim 1, wherein the first supplying section includes a container pervious to light for retaining a specimen for analysis of hemoglobin, a light source for irradiating the container with light, and a light receiving section for receiving light transmitted through the container.

7. A blood analyzer having a blood cell detector as recited in claim 6, further comprising a signal processing section for determining the amount of hemoglobin based on an intensity of the transmitted light.

8. A blood cell detector as set forth in claim 1, wherein the first and second supplying sections include first and second blood specimen containers, respectively.

9. A blood cell detector as set forth claim 8, wherein the first blood specimen container has an open top.

10. A blood cell detector as set forth claim 8 further comprising a cleaning liquid supplying section for supplying a cleaning liquid into the second blood specimen container.

11. A blood cell detector as set forth claim 10, wherein the cleaning liquid supplying section supplies the cleaning liquid into the second blood specimen container through a lower inlet of the second blood specimen container.

12. A blood cell detector as set forth in claim 1, wherein the first supplying section includes a blood specimen container for retaining the first blood specimen, and the second supplying section includes a nozzle for ejecting the second blood specimen into the orifice, and a sheath liquid supplying section for supplying a sheath liquid in which the ejected second blood specimen is enclosed to pass through the orifice.

13. A blood analyzer having a blood cell detector as recited in claim 1.

14. A blood analyzer as set forth in claim 13, further comprising a signal processing section for determining the number of white or red blood cells included in the first and second blood specimen.

15. A blood cell detector as set forth in claim 1, wherein the orifice has a diameter of 50 $\mu$m–100 $\mu$m.

16. A blood cell detector as set forth in claim 1, wherein the first and second supplying section include first and second blood specimen containers, respectively, and at least one of the first and second blood specimen containers has a inlet for receiving air to agitate a blood specimen retained in the container.

17. A blood analyzing method using a blood cell detector, comprising steps of:
  (a) causing a first specimen for analysis of white blood cells to pass through an orifice in a first direction,
  (b) detecting a change in impedance of the first specimen through first and second electrodes provided on opposite sides of the orifice,
  (c) determining the number of white blood cells based on the change in impedance,
  (d) causing a second specimen for analysis of red blood cells to pass through the orifice in a second direction that is an opposite direction to the first direction,
  (e) detecting a change in impedance of the second specimen through the first and second electrodes, and
  (f) determining the number of red blood cells based on the change in impedance.

18. The blood analyzing method of claim 17, wherein each of (a), (b), (c), (d), (e), and (f) is performed successively.

19. The blood analyzing method of claim 17, further comprising steps of:
  (g) supplying a diluent into a container pervious to light;
  (h) irradiating the container with light;
  (i) detecting a first intensity of light transmitted through the container;
  (j) discharging the diluent from the container;
  (k) supplying a third specimen for analysis of hemoglobin into the container,
  (l) irradiating the container with light,
  (m) detecting a second intensity of light transmitted through the container; and
  (n) determining the amount of hemoglobin based on the first and second intensities.

20. The blood analyzing method of claim 19, wherein each of (a), (b), (c), (d), (e), (f), (g), (h), (i), (j), (k), (l), (m) and (n) is performed successively.

21. The blood analyzing method of claim 19, wherein the first specimen and the third specimen are the same specimen.

* * * * *